United States Patent
Tipton et al.

(10) Patent No.: US 9,480,643 B2
(45) Date of Patent: Nov. 1, 2016

(54) IMPLANTABLE COMPOSITES AND IMPLANTS COMPRISING SAME

(75) Inventors: Arthur J. Tipton, Homewood, AL (US); Kevin W. Burton, Hoover, AL (US); Thomas C. Bischoff, Minneapolis, MN (US); William V. Ferris, Minneapolis, MN (US)

(73) Assignee: Surmodics Pharmaceuticals, Inc., Birmingham, AL (US)

( * ) Notice: Subject to any disclaimer, the term of this patent is extended or adjusted under 35 U.S.C. 154(b) by 487 days.

(21) Appl. No.: 12/644,094

(22) Filed: Dec. 22, 2009

(65) Prior Publication Data

US 2010/0158970 A1 Jun. 24, 2010

Related U.S. Application Data

(60) Provisional application No. 61/140,417, filed on Dec. 23, 2008.

(51) Int. Cl.
*A61K 9/00* (2006.01)

(52) U.S. Cl.
CPC .................................. *A61K 9/0024* (2013.01)

(58) Field of Classification Search
CPC .................................................. A61K 9/0024
See application file for complete search history.

(56) References Cited

U.S. PATENT DOCUMENTS

| | | |
|---|---|---|
| 4,020,558 A | 5/1977 | Cournut et al. |
| 4,241,489 A | 12/1980 | Manning |
| 4,704,692 A | 11/1987 | Ladner |
| 5,278,201 A | 1/1994 | Dunn et al. |
| 5,281,354 A | 1/1994 | Faber |
| 5,407,609 A | 4/1995 | Tice et al. |
| 5,599,552 A | 2/1997 | Dunn et al. |
| 5,599,852 A | 2/1997 | Scopelianos et al. |
| 5,702,716 A | 12/1997 | Dunn et al. |
| 5,702,717 A | 12/1997 | Cha et al. |
| 5,739,176 A | 4/1998 | Dunn et al. |
| 5,759,563 A | 6/1998 | Yewey et al. |
| 5,945,115 A | 8/1999 | Dunn et al. |
| 6,130,200 A | 10/2000 | Brodbeck et al. |
| 6,324,435 B1 * | 11/2001 | Shchervinsky et al. ...... 607/152 |
| 6,331,311 B1 | 12/2001 | Brodbeck et al. |
| 6,338,859 B1 | 1/2002 | Leroux et al. |
| 6,413,536 B1 | 7/2002 | Gibson et al. |
| 6,432,438 B1 | 8/2002 | Shukla |
| 6,468,961 B1 | 10/2002 | Brodbeck et al. |
| 6,469,132 B1 | 10/2002 | Eisenberg et al. |
| 6,471,987 B1 | 10/2002 | McBride-Sakal et al. |

(Continued)

FOREIGN PATENT DOCUMENTS

| | | |
|---|---|---|
| EP | 0306212 | 3/1989 |
| EP | 1 917 971 A1 | 5/2008 |

(Continued)

OTHER PUBLICATIONS

Mathisfun, rectangle, accessed Dec. 8, 2011, pp. 1.*

(Continued)

*Primary Examiner* — Ernst V Arnold
(74) *Attorney, Agent, or Firm* — Kagan Binder, PLLC

(57) ABSTRACT

Described herein are implantable composites, articles comprising the composites, implant devices comprising the composites, and methods of making and using same, including point of use methods.

17 Claims, 2 Drawing Sheets

(56) References Cited

U.S. PATENT DOCUMENTS

| | | | |
|---|---|---|---|
| RE37,950 E | 12/2002 | Dunn et al. | |
| 6,673,767 B1 | 1/2004 | Brodbeck et al. | |
| 6,846,352 B2 | 1/2005 | Yatake | |
| 6,846,795 B2 | 1/2005 | Lant et al. | |
| 6,849,426 B2 | 2/2005 | Chen et al. | |
| 6,852,816 B2 | 2/2005 | Lewis et al. | |
| 6,923,985 B2* | 8/2005 | Peterson et al. | 424/486 |
| 7,053,209 B1 | 5/2006 | Gibson et al. | |
| 7,122,205 B2 | 10/2006 | Peterson et al. | |
| 7,128,927 B1 | 10/2006 | Dunn | |
| 7,299,905 B2 | 11/2007 | Yamaguchi et al. | |
| 2002/0150622 A1 | 10/2002 | Philbrook et al. | |
| 2003/0068600 A1* | 4/2003 | Ellison | 433/174 |
| 2003/0114637 A1 | 6/2003 | Gogolewski | |
| 2003/0185872 A1 | 10/2003 | Kochinke | |
| 2003/0203991 A1 | 10/2003 | Schottman et al. | |
| 2004/0037885 A1 | 2/2004 | Seo et al. | |
| 2005/0079202 A1 | 4/2005 | Chen et al. | |
| 2005/0129732 A1 | 6/2005 | Rubsamen | |
| 2005/0267543 A1 | 12/2005 | Heruth et al. | |
| 2006/0147491 A1 | 7/2006 | DeWitt et al. | |
| 2007/0005094 A1 | 1/2007 | Eaton et al. | |
| 2007/0184084 A1 | 8/2007 | Chen et al. | |
| 2007/0190154 A1 | 8/2007 | Zeigerson | |
| 2007/0207189 A1 | 9/2007 | Belcheva et al. | |
| 2008/0125728 A1 | 5/2008 | Bischoff et al. | |
| 2008/0260796 A1 | 10/2008 | Bischoff et al. | |
| 2009/0124535 A1 | 5/2009 | Markland et al. | |
| 2009/0198197 A1 | 8/2009 | Bischoff et al. | |
| 2009/0306120 A1* | 12/2009 | Lim et al. | 514/291 |
| 2010/0098744 A1 | 4/2010 | Ferris et al. | |
| 2010/0198278 A1 | 8/2010 | Cobian et al. | |
| 2010/0203100 A1 | 8/2010 | Cobian et al. | |
| 2010/0247596 A1 | 9/2010 | Bischoff | |
| 2011/0098813 A1 | 4/2011 | Gibson | |

FOREIGN PATENT DOCUMENTS

| | | |
|---|---|---|
| EP | 2050474 | 4/2009 |
| WO | WO 2006124021 | 11/2006 |
| WO | PCT/US2008/012755 | 11/2008 |
| WO | WO-2009-064442 | 5/2009 |
| WO | PCT/US2009/069024 | 12/2009 |
| WO | WO-2010-075298 | 7/2010 |

OTHER PUBLICATIONS

Google, rectangle, accessed Dec. 8, 2011, pp. 1-2.*
Free Online Dictionary, Room Temperature, accessed Jun. 11, 2014, pp. 1-2.*
Kulkarni et al. "Poly(lactic acid) for surgical implants," Arch Surg., vol. 93(5):839-843, (1966).
Miller et al., "Degradation rates of oral restorable implants (polylactates and polyglycolates): Rate modification with changes in PLA/PGA copolymer ratios," J. Biomed. Mater. Res., vol. 11:711-719, (1977).
Sawhney et al., "Rapidly degraded terpolymers of d,l-lactide, glycolide and ε-caprolactone with increased hydrophilicity by copolymerization with polyethers," J. Biomed. Mater. Res., vol. 24:1397-1411, (1990).
Stolnik et al., "Polylactide-poly (ethylene glycol) micellar-like particles as potential drug carriers: Production, colloidal properties and biological performance," J. Drug Targeting, vol. 9:361-378, (2001).
Amendments before examination filed on Jul. 27, 2010 for EP Pat. App. No. 08850639.9, which claims priority to Intl. App. No. PCT/US08/012755, filed Nov. 12, 2008 (Inventor—Markland et al.; Applicant—Surmodics Pharmaceuticals, Inc.).
Intl. Report on Patentability issued on May 18, 2010 for Intl. App. No. PCT/US08/012755, filed Nov. 12, 2008 (Inventor—Markland et al.; Applicant—Surmodics Pharmaceuticals, Inc.).
Intl. Search Report with Written Opinion issued on Jan. 29, 2009 for Intl. App. No. PCT/US08/012755, filed Nov. 12, 2008 (Inventor—Markland et al.; Applicant—Surmodics Pharmaceuticals, Inc.).
Final Rejection issued on Jun. 3, 2011 for U.S. Appl. No. 12/269,135, filed Nov. 12, 2008 (Inventor—Markland et al.).
Intl. Report on Patentability issued on Jul. 7, 2011 for Intl. App. No. PCT/US09/069024, filed Dec. 21, 2009 (Inventor—Tipton et al.; Applicant—Surmodics Pharmaceuticals, Inc.).
Intl. Search Report with Written Opinion issued on Nov. 26, 2010 for Intl. App. No. PCT/US09/069024, filed Dec. 21, 2009 (Inventor—Tipton et al.; Applicant—Surmodics Pharmaceuticals, Inc.).
Non-Final Rejection issued on Aug. 3, 2011 for U.S. Appl. No. 12/643,558, filed Dec. 21, 2009 (Inventor—T. Tice).
Non-Final Rejection issued on Jun. 8, 2011 for U.S. Appl. No. 12/643,571, filed Dec. 21, 2009 (Inventor—T. Tice).
Response after Non-Final Rejection filed on Aug. 17, 2011 for U.S. Appl. No. 12/643,571, filed Dec. 21, 2009 (Inventor—T. Tice).
International Search Report from PCT/US2009/069024 mailed Nov. 26, 2010.
Hong et al. "Generating Elastic, Biodegradable Polyurethane/Poly(lactide-co-glycolide) Fibrous Sheets with Controlled Antibiotic Release via Two-Stream Electrospinning" Biomacromolecules (2008), 9, 1200-1207.
Gollwitzer et al. "Antibacterial poly(D,L-lactic acid) coating of medical implants using a biodegradable drug delivery technology" Journal of Antimicrobial Chemotherapy (2003) 51, 585-591.
Office Action mailed in U.S. Appl. No. 12/269,135 on Oct. 8, 2010.
Sakkas, P., The future: towards long acting atypical antipsychotics, Annals of General Hospital Psychiatry, Published Dec. 23, 2003.
Srisa-ard, Mangkorn, et al., Sytheis and characterization of a random terpolymer of L-lactide, ε-caprolactone and glycolide, Polymer International 50 (2001).
Response to Restriction Requirement filed Mar. 29, 2011 in U.S. Appl. No. 12/643,571.
Response to Non-Final Office Action filed Apr. 8, 2011 in U.S. Appl. No. 12/269,135.
Restriction Requirement mailed Feb. 2, 2011 in U.S. Appl. No. 12/643,571.
Response to Restriction Requirement filed Aug. 27, 2010 in U.S. Appl. No. 12/269,135.
U.S. Appl. No. 12/269,135, filed Nov. 12, 2008, Markland et al.
U.S. Appl. No. 13/022,720, filed Feb. 8, 2011, Markland et al.

* cited by examiner

IMPLANTABLE COMPOSITES AND IMPLANTS COMPRISING SAME

CROSS-REFERENCE TO RELATED APPLICATIONS

This application is based upon and claims the benefit of priority from prior U.S. Provisional Application No. 61/140,417, filed Dec. 23, 2008, the entire contents of which are incorporated herein by reference.

BACKGROUND

In medicine, certain disorders and conditions require medical implants. Medical implants are often used to replace a damaged biological tissue or fluid, augment or enhance a biological process, enhance the healing of a surgical site, deliver a drug to a localized site within a subject, or perform another biological or structural role. Implants can even be necessary to keep a patient alive. Unfortunately, problems can arise during an implant surgery, or after a patient has received the medical implant. In some instances, the implant can impair healing of the surgical site. For example, the surface of the implant can recruit cellular debris and other biological material that can become infected with bacteria, fungus, or other infectious agents. The subject's immune system can also recognize the implant as a foreign body, and attempt to fight the implant using natural defenses. This often lowers the strength of the subject's immune system and can lead to further serious problems, such as periprosthetic infections, or other infections at or near the surgical implant site.

Accordingly, it can also be desirable to deliver a bioactive agent at or near the tissue adjacent the implant site. Such a bioactive agent can help prevent at least some of the aforementioned problems associated with implants, or enhance the function of the implant itself. Unfortunately, configuring each implant to be capable of locally delivering a bioactive agent is not always possible or practical. For example, regulations for the manufacture of drug products differ significantly from the regulations for the manufacture of medical devices.

As such, a need exists for composites that can be applied to an implant or implanted into a subject that effectively provide a bioactive agent at or near tissue adjacent the implant site. These needs and other needs are satisfied by the present invention.

SUMMARY

Described herein are implantable composites, kits and articles comprising the implantable composites, and implant devices comprising the implantable composites. In one aspect, disclosed are point of use applications, wherein a bioactive agent is applied to a medical device close to the time of use, which allows for the separate and more rapid development of the bioactive agent and the implant device, such that the quality or efficacy of the final implant device is not unduly compromised.

In one aspect, disclosed is an implantable composite comprising: a tacky biocompatible polymer film comprising a releasable bioactive agent; and a release liner affixed or adhered to the tacky biocompatible polymer film.

In another aspect, disclosed is an article comprising a plurality of implantable composites that each comprise a biocompatible polymer film comprising a releasable bioactive agent; and one or more release liners affixed or adhered to each implantable composite.

In another aspect, disclosed is an implant device having a first implant device surface comprising an implantable composite affixed or adhered to at least a portion of the first implant device surface, wherein the implantable composite comprises a biocompatible polymer film comprising a releasable bioactive agent.

Also disclosed are methods of applying an implantable composite to an implant device, the method comprising securing an implantable composite onto a surface of an implant device, substantially close to the time when the implant device is implanted in a subject.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
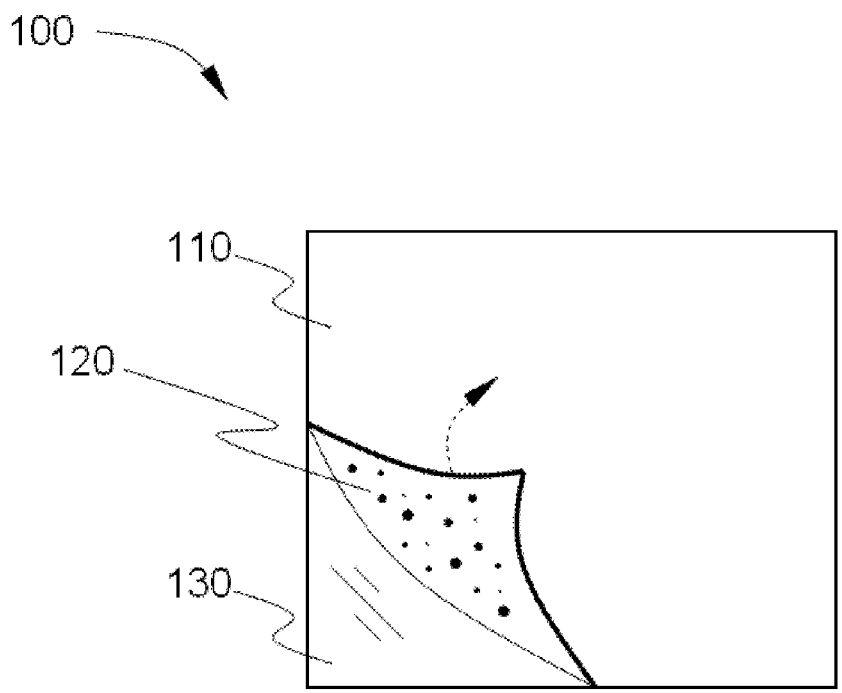
FIG. 1A is a drawing of an exemplary implantable composite.

Before the present compounds, compositions, composites, articles, devices and/or methods are disclosed and described, it is to be understood that the aspects described below are not limited to specific compounds, compositions, composites, articles, devices, methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

The term "tacky polymer" refers to a polymer that has at least one surface that is tacky at room temperature. In one aspect, a "tacky polymer" can act like an adhesive. To that end, a "tacky polymer" can be designed to be capable of adhering to a material or article, such as an implant device, release liner, or tissue or fluid of a subject.

The term "biocompatible" refers a substance that is substantially non-toxic to a subject.

"Biodegradable" is generally referred to herein as a material that will erode to soluble species or that will degrade under physiologic conditions to smaller units or chemical species that are, themselves, non-toxic (biocompatible) to the subject and capable of being metabolized, eliminated, or excreted by the subject.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. A "releasable bioactive agent" is one that can be released from a disclosed polymer film. Bioactive agents also include those substances which affect the structure or function of a subject, or a pro-drug, which becomes bioactive or more bioactive after it has been placed in a predetermined physiological environment.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are implantable composites that can be applied to an implant device, or to a tissue or fluid of a subject. The implantable composites can release a bioactive agent into the subject. The composites described herein allow for controlled-release, extended-release, modified-release, sustained-release, pulsatile-release, delayed-release, or programmed-release of the bioactive agent.

In one aspect, the implantable composite comprises a biocompatible polymer film having at least a first surface, and a releasable bioactive agent therein the composite; an adhesive on at least a portion of the first surface; and a release liner affixed to the adhesive.

The implantable composite can have any desired shape. For example, the implantable composite can be substantially spherical, cylindrical, planar, or cubical. A planar implantable composite can be substantially square, rectangular, circular, triangular, among other shapes. In one aspect, the implantable composite can be square or rectangular. In a further aspect, the implantable composite has a shape that is non-rectangular. As shown in FIG. 1A, for example, an implantable composite 100 can have a substantially squared shape, with the length of the composite approximately equal to the width of the composite. As shown in FIG. 1A, the implantable composite 100 comprises a polymer film 110 having at least a first surface 120. The polymer film 110 comprises the releasable bioactive agent (not shown). An adhesive (not shown) can be optionally present on at least a portion of a first surface 120, or on the entire first surface 120, of the polymer film. The adhesive allows the polymer film to adhere to an implant device, or to an internal tissue or fluid of a subject. Prior to the implantable composite being implanted in a subject, the adhesive can be at least partially, or fully, covered with a release liner. As shown in FIG. 1A, a release liner 130 is affixed to the adhesive present on the first surface 120 of the polymer film. In other alternative embodiments, the release liner is not present.

The implantable composites can have any desired size. In general, the size selection of the implantable composite can be influenced by the desired loading of the bioactive agent. Generally, the more bioactive agent that is desired, the larger the implantable composite will be. The size can also be selected so as to provide the desired release properties of the polymer film. In addition, when the implantable composite is applied to an implant device, the size of the implant device can be of importance when selecting the size of the implantable composite. For example, it can be desirable for portions of the implant device surface to remain exposed. In these instances, the size of the implant can be selected so as to not completely cover the implant device surface.

Implantable composites can occupy any desired volume, for example, volumes of from about 0.1 cm$^3$ to about 30 cm$^3$, including, for example, 1, 2, 3, 4, 5, 6, 7, 10, 12, 14, 15, 18, 20, 22, 25, 28, and 29 cm$^3$. Smaller implantable composites, for example, can occupy a volume of from about 0.1 mm$^3$ to about 100 mm$^3$, including, for example, 0.5, 1, 3, 5, 7, 9, 10, 12, 15, 20, 25, 30, 35, 40, 45, 50, 60, 70, 80, 85, or 90 mm$^3$. In other aspects, the implantable composite can be shaped so as to have a length and a width. The length can be greater than, less than, or equal to, the width of the implantable composite. Suitable lengths and widths include, for example, 0.1 cm, or smaller, to about 30 cm, or larger, including without limitation 1, 2, 3, 4, 5, 6, 7, 10, 12, 14, 15, 18, 20, 22, 25, 28, and 29 cm. For example, the implantable composite can have an area of from about 0.1 cm×0.1 cm to about 30 cm×30 cm, including, for example, 0.1 cm×0.5 cm, 1 cm×1 cm, 1 cm×1.5 cm, 2 cm×2 cm, 2 cm×0.5 cm, 5 cm×5 cm, 5 cm×2 cm, 10 cm×10 cm, 10 cm×5 cm, 15 cm×10 cm, 15 cm×15 cm, 20 cm×20 cm, 20 cm×15 cm, 25 cm×25 cm, or 30 cm×20 cm. Smaller implantable composites can have a length or width from about 0.1 mm, or smaller, to about 1 mm, or larger, including, for example, 0.2, 0.3, 0.4, 0.5, 0.6, 0.7, 0.8, or 0.9 mm. Such implants can have an area of from about 0.1 mm×0.1 mm, 0.2 mm×0.1 mm, 0.3 mm×0.3 mm, 0.3 mm×0.2 mm, 0.5 mm×0.5 mm, 0.5 mm×0.2 mm, 0.8 mm×0.8 mm, or 0.9 mm×0.9 mm.

In one aspect, wherein if the implantable composite has a length dimension substantially larger than a width dimension and a width dimension substantially larger than a thickness dimension, then the width dimension is less than about 2 mm. In a further aspect, if the implantable composite has a length dimension substantially larger than a width dimension and a width dimension substantially larger than a thickness dimension, then the width dimension is less than about 2 mm. In a still further aspect, the implantable composite can have a length dimension that is substantially the same as the width dimension. In a further aspect, the implantable composite does not have a length dimension substantially larger than a width dimension and a width dimension substantially larger than a thickness dimension.

Figure 1B:
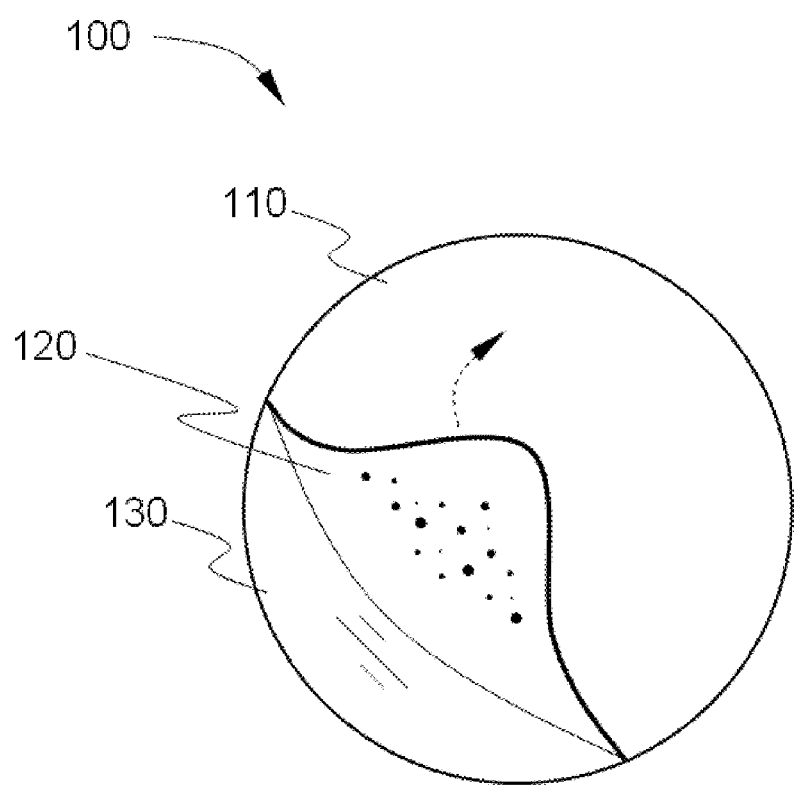
FIG. 1B is a drawing of another exemplary implantable composite.

In still other aspects the implantable composite can be a non square or non rectangular shape, and as such comprise one or more dimensions that is from about 0.1 cm to about 30 cm, including without limitation 1, 2, 3, 4, 5, 6, 7, 10, 12, 14, 15, 18, 20, 22, 25, 28, and 29 cm. A triangle, for example, can comprise one or more dimensions in the aforementioned size ranges. In further aspects, the implantable composites can be substantially circular (e.g., as shown in FIG. 1B), and comprise a diameter from about 0.1 cm to about 30 cm, including, for example, 1, 2, 3, 4, 5, 6, 7, 10, 12, 14, 15, 18, 20, 22, 25, 28, and 29 cm.

The polymer film can have any desired thickness. In one aspect, the polymer film is a thin film having a thickness of from about 1 nm, or less, to about 1000 nm, including without limitation those films having thicknesses of about 5 nm, 20 nm, 50 nm, 150 nm, 200 nm, 300 nm, 500 nm, 800 nm, or 900 nm. In a further aspect, the film has a thickness greater than about 1000 nm, including without limitation those films having thicknesses of from about 1000 nm to about 50 cm, or greater. For example, the film can have a thickness of about 2000 nm, 0.1 cm, 0.5 cm, 1 cm, 5 cm, 20 cm, 30 cm, 40 cm, or 50 cm. It is to be understood that the film does not have to be, but can be, planar. Thus, in various aspects, the film may have varying heights at different regions of the film. As such, the film can comprise any shape, as discussed above, depending on the desired shape of the implantable composite.

Figure 2:
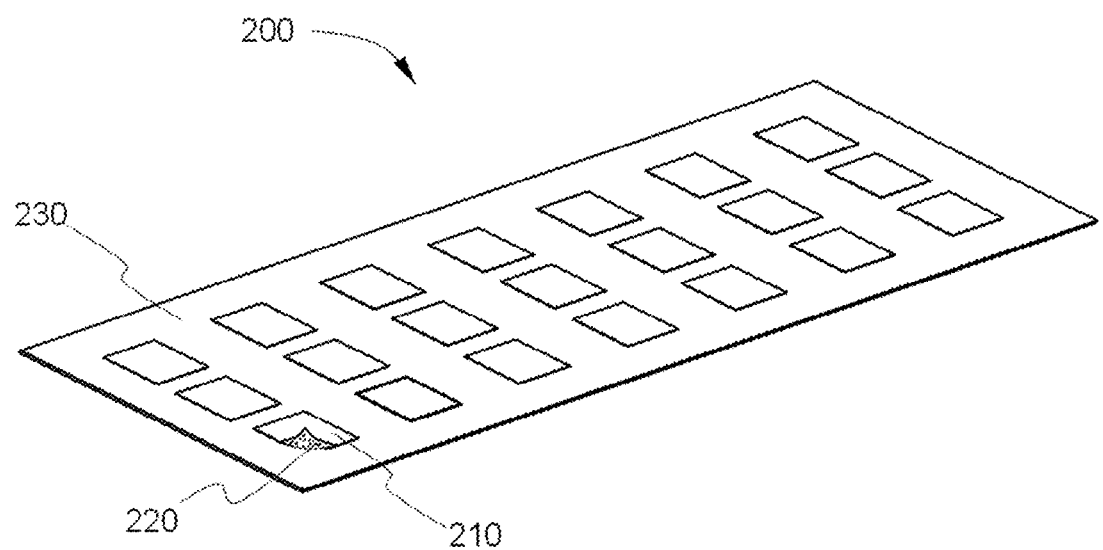
FIG. 2 is a drawing of an exemplary article comprising a plurality of implantable composites.

Also disclosed are articles and kits comprising the implantable composites. An exemplary article 200 is shown in FIG. 2, which shows a planar release liner 230 comprising a plurality of implantable composites. As shown, each implantable composite comprises a polymer film 210 having at least a first surface 220 that optionally comprises an adhesive (not shown). The adhesive can be affixed to a release liner 230. In this example, the article comprises a plurality of implantable composites that all share the release liner 230. However, alternate embodiments include kits that are a package of a plurality of implantable composites, such as those depicted in FIG. 1A and FIG. 1B, in a package. Also disclosed are kits comprising a mixture of the same or different implantable composites. For example, the kit can comprise several sets of implantable composites, each having a different size. Such a kit may be useful for point of use applications of the implantable composites, wherein one kit, for example, can provide implantable composites that are compatible in size with a number of different implant devices.

The polymer used with the implantable composites can be any suitable biocompatible and biodegradable or non-biodegradable polymer. The polymers disclosed herein can be homopolymers or copolymers. The polymers can be block or blocky co- or ter-polymers, random co- or ter-polymers, star polymers, or dendrimers. Any desired molecular weight polymer can be used, depending on the desired properties of the implantable composite. In certain aspects, if a high strength implantable composite is desired, then high molecular weight polymers can be used, for example, to meet strength requirements. In other aspects, low or medium molecular weight polymers can be used when, for example, when resorption time of the polymer, rather than material strength is desired.

The molecular weight of the polymer can be selected so as to provide a desired property of the implantable composite. In certain aspects, the polymer film can be provided by forming a film of the polymer. In such aspects, the molecular weight should be high enough so that it forms satisfactory films. Usually, a molecular weight greater than 10,000 daltons can achieve this. However, since the properties of the film are also partially dependent on the particular polymeric material being used, it is difficult to specify an appropriate molecular weight range for all polymers. The molecular weight of a polymer is also important from the point of view that molecular weight influences the biodegradation rate of the polymer. For a diffusional mechanism of bioactive agent release, the polymer should remain intact until all of the drug is released from the polymer and then degrade. The drug can also be released from the polymer as the polymer bioerodes. By an appropriate selection of polymeric materials a polymer formulation can be made such that the resulting biocompatible polymer exhibits both diffusional release and biodegradation release properties. Molecular weights can be measured by methods known in the art, including gel permeation chromatography, viscosity, light-scattering, among other methods.

The biodegradable polymer film can be formulated so as to degrade within a desired time interval, once present in a subject. In some aspects, the time interval can be from about less than one day to about 1 month. Longer time intervals can extend to 6 months, including for example, polymer matrices that degrade from about ≥0 to about 6 months, or from about 1 to about 6 months. In other aspects, the polymer can degrade in longer time intervals, up to 2 years or longer, including, for example, from about ≥0 to about 2 years, or from about 1 month to about 2 years.

The desired bioactive agent release mechanism can influence the selection of the polymer. A biocompatible polymer can be selected so as to release or allow the release of a bioactive agent therefrom at a desired lapsed time after the implantable composite has been implanted into a subject. For example, the polymer can be selected to release or allow the release of the bioactive agent prior to the bioactive agent beginning to diminish its activity, as the bioactive agent begins to diminish in activity, when the bioactive agent is partially diminished in activity, for example at least 25%, at least 50% or at least 75% diminished, when the bioactive agent is substantially diminished in activity, or when the bioactive agent is completely gone or no longer has activity.

In one aspect, the polymer can be one or more of polyesters, polyhydroxyalkanoates, polyhydroxybutyrates, polydioxanones, polyhydroxyvalerates, polyanhydrides, polyorthoesters, polyphosphazenes, polyphosphates, polyphosphoesters, polydioxanones, polyphosphoesters, polyphosphates, polyphosphonates, polyphosphates, polyhydroxyalkanoates, polycarbonates, polyalkylcarbonates, polyorthocarbonates, polyesteramides, polyamides, polyamines, polypeptides, polyurethanes, polyalkylene alkylates, polyalkylene oxalates, polyalkylene succinates, polyhydroxy fatty acids, polyacetals, polycyanoacrylates, polyketals, polyetheresters, polyethers, polyalkylene glycols, polyalkylene oxides, polyethylene glycols, polyethylene oxides, polypeptides, polysaccharides, or polyvinyl pyrrolidones. Other non-biodegradable but durable polymers include without limitation ethylene-vinyl acetate co-polymer, polytetrafluoroethylene, polypropylene, polyethylene, and the like. Likewise, other suitable non-biodegradable polymers include without limitation silicones and polyurethanes.

In a further aspect, the polymer can be a poly(lactide), a poly(glycolide), a poly(lactide-co-glycolide), a poly(caprolactone), a poly(orthoester), a poly(phosphazene), a poly(hydroxybutyrate) or a copolymer containing a poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

In a still further aspect, useful biocompatible polymers are those that comprise one or more residues of lactic acid, glycolic acid, lactide, glycolide, caprolactone, hydroxybutyrate, hydroxyvalerates, dioxanones, polyethylene glycol (PEG), polyethylene oxide, or a combination thereof. In a still further aspect, useful biocompatible polymers are those that comprise one or more residues of lactide, glycolide, caprolactone, or a combination thereof.

In one aspect, useful biodegradable polymers are those that comprise one or more blocks of hydrophilic or water soluble polymers, including, but not limited to, polyethylene glycol, (PEG), or polyvinyl pyrrolidone (PVP), in combination with one or more blocks another biocompatible or biodegradable polymer that comprises lactide, glycolide, caprolactone, or a combination thereof.

In specific aspects, the biodegradable polymer can comprise one or more lactide residues. To that end, the polymer can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

When the biodegradable polymer is poly(lactide-co-glycolide), poly(lactide), or poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

In a further aspect, the polymer can be a poly(caprolactone) or a poly(lactide-co-caprolactone). In one aspect, the polymer can be a poly(lactide-caprolactone), which, in various aspects, can be 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

In one aspect, the polymer film can comprise a terpolymer. In one aspect, the terpolymers are those terpolymers disclosed in U.S. patent application Ser. No. 12/269,135, filed Nov. 12, 2008, (U.S. Patent Publication No. 2009/0124535) which is incorporated herein by this reference for all of its teachings of terpolymers and is considered part of this disclosure. In the disclosed terpolymers, lactide can be present in an amount of from about 10 to about 60 mole percent. For example, the lactide can be present in an amount of from about 10 to about 30 mole percent, from about 20 to about 40 mole percent, from about 30 to about 50 mole percent, from about 40 to about 60 mole percent, from about 50 to about 60 mole percent, from about 10 to about 20 mole percent, from about 20 to about 30 mole percent, from about 25 to about 45 mole percent, from about 45 to about 60 mole percent, from about 10 to about 25 mole percent, from about 12 to about 18, or from about 13 to about 16 mole percent. In other examples, lactide can be present in about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mole percent, where any of the stated values can form an upper or lower endpoint of a range. In a specific example, the disclosed terpolymers comprise about 15 mole % of lactide. In the disclosed terpolymers, glycolide can be present in an amount of from about 10 to about 40 mole percent. For example, the glycolide can be present in an amount of from about 10 to about 20, from about 20 to about 30, from about 30 to about 40, from about 15 to about 25, from about 25 to about 35, from about 22 to about 28, or from about 24 to about 26 mole percent. In other examples, glycolide can be present in about 10, 11, 12, 13, 14, 15, 16, 17, 18, 19, 20, 21, 22, 23, 24, 25, 26, 27, 28, 29, or 30 mole percent, where any of the stated values can form an upper or lower endpoint of a range. In a specific example, the disclosed terpolymers comprise about 25 mole % of glycolide. In the disclosed terpolymers, ε-caprolactone can be present in an amount of from about 20 to about 70 mole percent. For example, the ε-caprolactone can be present in an amount of from about 20 to about 50 mole percent, from about 30 to about 60 mole percent, from about 40 to about 70 mole percent, from about 20 to about 40 mole percent, from about 20 to about 30 mole percent, from about 30 to about 50 mole percent, from about 40 to about 60 mole percent, from about 50 to about 70 mole percent, from about 40 to about 50, from about 50 to about 60, from about 60 to about 70, from about 40 to about 55, from about 45 to about 60, from about 45 to about 65, from about 55 to about 65, or from about 58 to about 63 mole percent. In other examples, ϵ-caprolactone can be present in about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mole percent, where any of the stated values can form an upper or lower endpoint of a range. In a specific example, the disclosed terpolymers comprise about 60 mole % of ϵ-caprolactone.

It is understood that any combination of the aforementioned biodegradable polymers can be used, including, but not limited to, copolymers thereof, mixtures thereof, or blends thereof. Likewise, it is understood that when a residue of a biodegradable polymer is disclosed, any suitable polymer, copolymer, mixture, or blend, that comprises the disclosed residue, is also considered disclosed. To that end, when multiple residues are individually disclosed (i.e., not in combination with another), it is understood that any combination of the individual residues can be used.

In one aspect, an adhesive can be present on a surface of a disclosed implantable composite. In certain aspects, the polymer film itself can be a tacky polymer film, which functions as an adhesive to which a release liner, implant device, or tissue or fluid of the subject can directly adhere. Methods of making the above disclosed polymers tacky are known in the art. Additives for example, can be added to provide a tacky polymer that can be adhesive. In one aspect, tacky polymers can be those that comprise a $T_g$ of less than about room temperature, including those polymers disclosed above which have glass transition temperatures of less than about room temperature.

In various aspects, the polymer film does not have to be, but can be, comprised of a tacky polymer film. Thus, in a further aspect, an adhesive, separate from the polymer film, can be on a polymer film. The adhesive can be any desired adhesive. Suitable adhesives include without limitation thermoplastics, glycoproteins, mucopolysaccharides, bioadhesives, carbohydrates, starches, dextrin, sugars, gelatin, epoxy, acrylics, rubber, silicones, polyurethanes, pressure sensitive adhesives, polyesters, polyethers, polychloroprene, natural gums, peroxides, silanes, isocyanates, or combinations, mixtures, and blends thereof.

In one aspect, the adhesive can be a biocompatible or biodegradable adhesive, including without limitation, poly (lactide-co-caprolactone), poly(glycolide-co-caprolactone), or combinations, mixtures, and blends thereof.

The adhesive can be applied to the first surface of the polymer film through methods known in the art. Adhesives can be applied, for example, through spin-coating, drop-casting, brushing, or spraying an adhesive composition onto the first surface of the polymer film.

As discussed above, in one aspect, the implantable composite comprises a release liner. The release liner can be any suitable release liner. The release liner is typically a temporary release liner that is removed from the polymer film of the implantable composite prior to the implantable composite being implanted into a subject. As such, it is preferred that the temporary release liner not leave behind any material in a quantity that could be harmful to a subject.

Suitable release liners are those that are made of materials that permit the release liner to be easily stripped or peeled away from the adjacent adhesive. Exemplary release liners are those that are comprised of paper and/or a plastic material. Typically, such release liners are made from polymers such as polyesters or polyethylenes which are coated with materials such as silicone or fluorinated hydrocarbons that reduce the adhesiveness between the release liner and the adjacent adhesive. Other suitable release liners include paper, such as kraft paper, that is covered with a silicone material, which permits the easy release of the liner from the adhesive. Release liner materials are available commercially, for example, polyethylene is commercially available from 3M®.

In one aspect, the release liner is the polymer film. That is, the first surface of the polymer film is adhered to an opposing second surface of the polymer film with an adhesive. For example, the implantable composite can be configured as a roll of tape, wherein the second opposing surface of the polymer film functions as the release liner. In other aspects, the release liner is not the polymer film. That is, the first surface of the polymer film is not adhered to an opposing second surface of the polymer film. Thus, in some aspects, the implantable composite is not a roll of tape, wherein the second opposing surface of the polymer film functions as the release liner.

As discussed above, the implantable composite comprises a bioactive agent. The bioactive agent can be a releasable bioactive agent, i.e., a bioactive agent that can be released from the polymer film. In certain aspects, the bioactive agent can be in or on the polymer film.

Various forms of the bioactive agent can be used, which are capable of being released from polymer film into adjacent tissues or fluids. To that end, a liquid or solid bioactive agent can be incorporated into the implantable composites described herein. The bioactive agents are at least very slightly water soluble, and preferably moderately water soluble. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents that incorporated into systems herein include, but are not limited to, peptides, proteins such as hormones, enzymes, antibodies and the like, nucleic acids such as aptamers, iRNA, DNA, RNA, antisense nucleic acid or the like, antisense nucleic acid analogs or the like, low-molecular weight compounds, or high-molecular-weight compounds. Bioactive agents contemplated for use in the disclosed implantable composites include anabolic agents, antacids, anti-asthmatic agents, anti-cholesterolemic and anti-lipid agents, anti-coagulants, anti-convulsants, anti-diarrheals, anti-emetics, anti-infective agents including anti-bacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents in the implantable composites include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

The implantable composite can comprise a large number of bioactive agents either singly or in combination. Other bioactive agents include but are not limited to analgesics such as acetaminophen, acetylsalicylic acid, and the like; anesthetics such as lidocaine, xylocalne, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxam®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a specific aspect, the bioactive agent comprises at least one of an antibiotic, antimicrobial, a growth factor, a growth inhibitor, an immunomodulator, a steroid, or an anti-inflammatory, including without limitation any of those disclosed above.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, or a combination thereof. In one aspect, the bioactive agent can be a combination of Rifampicin (Rifampin in U.S.) and Minocycline.

It is contemplated that other components such as, for example, excipients, pharmaceutically carriers or adjuvants, microparticles, and the like, can be combined with the polymer film and/or the bioactive agent. Thus, in certain aspects, the bioactive agent can be present as a component in a pharmaceutical composition. Pharmaceutical compositions can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the bioactive agent into association with a liquid carrier or a finely divided solid carrier, or both. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, a salt, a water-soluble polymer such as polyethylene glycol, a protein, polysaccharide, or carboxymethyl cellulose, a surfactant, a plasticizer, a high- or low-molecular-weight porosigen such as polymer or a salt or sugar, or a hydrophobic low-molecular-weight compound such as cholesterol or a wax.

In certain aspects, the polymer and bioactive agent are combined or admixed to form a blend or admixture. Admixing methods can be performed using techniques known in the art. For example, the polymer and bioactive agent can be dry blended (i.e., mixing of particulates of the polymer and the agent) using, for example, a Patterson-Kelley V-blender, or granulated prior to processing.

In one aspect, the processing of the admixture can be performed under conditions such that the agent is intimately mixed or dispersed throughout the polymer film. Alternatively, the processing of the admixture can be performed under conditions such that the agent is localized on or in only a portion or portions of the polymer film. To that end, the polymer film can include areas that are rich in bioactive agent, and areas that are not as rich. The admixture can be processed by a variety of techniques, such as, for example, melt extruding, injection molding, compression molding, or roller compacting the admixture into a desired shape or structure.

Other suitable pharmaceutical carriers include without limitation microparticles. The term "microparticle" is used herein to refer generally to a variety of substantially structures having sizes from about 10 nm to 2000 microns (2 millimeters) and includes microcapsule, microsphere, nanoparticle, nanocapsule, nanosphere as well as particles, in general, that are less than about 2000 microns (2 millimeters). The microparticle can contain and effect the release of the bioactive agent from the polymer film.

The microparticle can be comprised of any of those polymers mentioned above or any polymer used in the microparticle art. In general, the above mentioned polymers can be cross-linked to a certain level, which thereby can form a microparticle of the polymer, as is known in the art. When a microparticle is present in the polymer film, the microparticle can be the same or different as the polymer comprising the bulk of the polymer film. The polymer film can comprise any desired amount of microparticles, including, for example, from about 1 weight % to about 95 weight %, including 5, 10, 20, 30, 40, 50, 60, 70, 80, and 90 weight %, relative to the weight of the total polymer film. The microparticle can be combined with the polymer film through known methods.

In one aspect, the disclosed microparticles can have an average or mean particle size of from about 20 microns to about 125 microns. In one embodiment the range of mean particle size is from about 40 microns to about 90 microns. In another embodiment the range of mean particle sizes is from about 50 microns to about 80 microns. Particle size distributions are measured by laser diffraction techniques known to those of skill in the art.

In a further aspect, the bioactive agent can be encapsulated, microencapsulated, or otherwise contained within a microparticle. The microparticle can modulate the release of the bioactive agent. The microparticle can comprise any desired amount of the bioactive agent. For example, the microparticle can comprise 1%, 5%, 10%, 20%, 30%, 40%, 50%, 60%, 70%, 80%, 90%, 95% by weight bioactive agent, relative to the weight of the microparticle, including any range between the disclosed percentages.

The microparticles can be made using methods known in the art, including, for example, those methods disclosed in U.S. Patent Publication No. 2007/0190154, published Aug. 16, 2007, and U.S. Pat. No. 5,407,609 to Tice et al., both of which are incorporated herein in their entirety by this reference for teachings of microparticle preparation methods. As will be apparent, depending upon processing conditions, the polymer used as a starting material in the admixing step may or may not be the same polymer present in the final implantable composite. For example, the polymer during processing may undergo polymerization or depolymerization reactions, which ultimately can produce a different polymer that was used prior to processing. Thus, the term "polymer" as used herein covers the polymers used as starting materials as well as the final polymer present in the device produced by the methods described herein.

Also disclosed are implant devices comprising the implantable composites. The term "device" is any formulation or article that is greater than 1 mm in length in at least one dimension of the device. The device can comprise a disclosed implantable composite. In a further aspect, the device has one dimension that is from 1 mm to 50 mm, 1.2 mm to 45 mm, 1.4 mm to 42 mm, 1.6 mm to 40 mm, 1.8 mm to 38 mm, or 2.0 mm to 36 mm, 5.0 mm to 33 mm, or 10 mm to 30 mm. In a further aspect, the device has one dimension that is greater than 3 cm, even up to or greater than 10 cm, 20 cm, or even 30 cm.

In one aspect, the implant device comprises at least a first implant device surface comprising an implantable composite on at least a portion thereof, wherein if the implantable composite has a length dimension substantially larger than a width dimension and a width dimension substantially larger than a thickness dimension, then the width dimension is less than about 2 mm.

The implant device can comprise any shape, such as a rod, a fiber, a cylinder, a bead, a ribbon, a disc, a wafer, a free-formed shaped solid, or a variety of other shaped solids. The device can have any regular or irregular shape and can have any cross section like circular, rectangular, triangular, oval, and the like. In a further aspect, the device comprises a cylindrical shape, such as a typical shape of an implantable pump.

The implant can be comprised of any suitable material, such as a metal (e.g., titanium), metal composite, organic material, polymeric, or even ceramic material. The surface of the implant can be any shaped surface, and may have a porous, beaded or meshed ingrowth surface, as can be present in certain implants.

The implant device can be any type of medical implant. The implant devices can include, for example, implants for drug delivery, including drug delivery pumps; orthopedic implants, including spinal implants, implants for osseointegration or bone repair; medical stents, including stents with inherent drug delivery capability; prosthetic implants, including breast implants, muscle implants, and the like; dental implants; ear implants, including cochlear implants and hearing devices; cardiac implants including pacemakers, catheters, etc.; space filling implants; bioelectric implants; neural implants; internal organ implants, including dialysis grafts; defibrillators; monitoring devices; recording devices; stimulators, including deep brain stimulators, nerve stimulators, bladder stimulators, and diaphragm stimulators; implantable identification devices and information chips; artificial organs; drug administering devices; implantable sensors/biosensors; screws; tubes; rods; plates; or artificial joints.

In a further aspect, the implant device can be at least one of a pump, pacemaker, defibrillator, or stimulator, including deep brain stimulators, nerve stimulators, bladder stimulators, and diaphragm stimulators.

Figure 3:
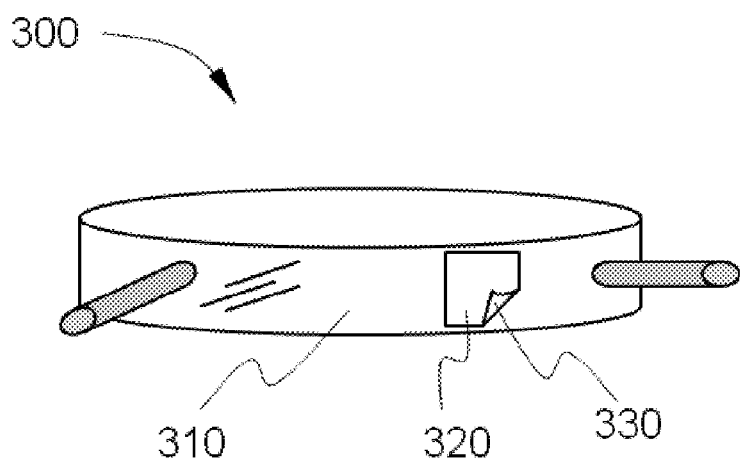
FIG. 3 is a drawing of an exemplary implant device comprising an implantable composite.

With reference to FIG. 3 an implant device 300 comprises a first implant device surface 310 that comprises an implantable composite comprised of a polymer film 320, which is adhered to the first implant device surface by a first surface 330 of the polymer film 320. The device shown in the FIG. 3 is an implantable pump. Once the implant device is present in a subject, the polymer film can degrade, allowing the bioactive agent to be released in or near the tissue that is adjacent the implant site. If desired, a plurality of implantable composites can be applied to the implant device.

Other implant devices that may benefit when used with the disclosed implantable composites include those with one or more active surfaces, e.g., a surface that enhances a connection between a tissue or fluid and the implant device, or a surface that allows for or enhances wound healing. To that end, the disclosed implantable composites can be effective when applied to only a portion of the implant device, allowing for any active surface to remain exposed and functional when the implant device is implanted in a subject.

As discussed above, it can be desirable to deliver a bioactive agent at or near the tissue adjacent an implant site. The bioactive agent can help prevent some of the problems associated with implants, such as infection, or enhance the function of the implant itself. It can also be desirable to avoid pre-manufacturing an implant device with bioactive agent releasing capability, as discussed above. It should be appreciated that the composites, methods, and kits and articles disclosed herein can allow for a point of use application of an implantable composite onto the surface of an implant device, thus obviating the need to pre-manufacture implant devices having bioactive agent releasing capability.

In one aspect, an implantable composite can be applied to an implant device surface close to or during the time of use. For example, an implantable composite can be applied to an implant device by securing the implantable composite onto the surface of the implant device, substantially close to the time when the implant device is implanted in a subject. In one aspect, the implantable composite can be applied to an implant device in an operating suite, for example, by a physician or nurse.

The implantable composite can be secured to the surface of the implant device prior to or after the time when the implant device is implanted in the subject. In one aspect, the implant device comprising the implantable composite can be implanted into the subject. In a further aspect, the implant device can be implanted into the subject, and then the implantable composite can be applied to the surface of the implant device. When implanting smaller implants, it may be beneficial to first apply the implantable composite to the implant device surface.

In one aspect, the implantable composite can be secured to the surface of the implant device on the same day (i.e., within 24 hours) of the implant surgery, including, for example, within 23 hours, 20 hours, 15 hours, 10 hours, 5 hours, 3 hours, 2 hours, 1 hour, 30 minutes, 15 minutes, 10 minutes, 5 minutes, 2 minutes, 30 seconds, or during the implant surgery itself.

If desired, the implantable composite itself, with or without an implant device, can be implanted onto or in a tissue or fluid of a subject. In one aspect, the implantable composite can be implanted onto or in a tissue or fluid that is near or adjacent to an implant site, i.e., a site where an implant device has been implanted, or near or adjacent to a desired implant site.

Typically, before applying the implantable composite to the implant device, the implant device surface can be cleaned or treated to remove any surface contaminants and to promote good adhesion of the polymer film. For example, the implantable composite and/or the implant device can be sterilized e.g. by autoclaving under water steam. The implantable composite or implant device comprising the implantable composite can then be implanted into the subject using known surgical techniques. In certain aspects, it can be desirable to store the implantable composites or kits and articles comprising the composites in a sterilized container or package. In one aspect, the kit can comprise a sterilized package of the implantable composites.

In one aspect, the disclosed methods can be used with implantable composites comprising a releasable bioactive agent. In a further aspect, the methods can be used with implantable composites comprising a polymer film having at least a first surface, and a releasable bioactive agent; and an adhesive on at least a portion, or all, of the first surface. In a still further aspect, the methods can be used with implantable composites comprising a polymer film having at least a first surface, and a releasable bioactive agent, with an adhesive on at least a portion, or all, of the first surface, and a release liner affixed to the adhesive; wherein the release liner is removed from the adhesive before the implantable composite is secured onto the surface of the implant device. The release liner can be removed by peeling the release liner away from the polymer film and/or adhesive, or by pealing the polymer film away from the release liner. The implantable composite can then be applied to the surface of the implant, or to the tissue or fluid of the subject, by contacting the surface of the implant with the contacting side of the implantable composite and optionally applying pressure to promote good adhesion. If a pressure sensitive adhesive is used, it can be desirable to apply pressure to the implantable composite to promote good adhesion of the composite onto the implant device surface.

The implant device can be implanted in any desired subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. An implantable composite comprising: a solid tacky biocompatible polymer film comprising a releasable bioactive agent; and a release liner affixed or adhered to the solid tacky biocompatible polymer film; wherein the solid tacky biocompatible polymer film comprises an adhesive polymer having a $T_g$ less than room temperature and comprises a terpolymer of lactide, glycolide and caprolactone residues, and wherein the amount of lactide residue in the terpolymer is from 10 to 31 mole percent, the amount of glycolide in the terpolymer is from 10 to 40 mole percent, and the amount of caprolactone in the terpolymer is at least 49 mole percent.

2. The implantable composite of claim 1, wherein the implantable composite has a length dimension and a width dimension, wherein the length dimension is substantially the same as the width dimension.

3. The implantable composite of claim 1, wherein the implantable composite has a shape that is not rectangular.

4. The implantable composite of claim 1, wherein the bioactive agent is encapsulated within a microparticle.

5. The implantable composite of claim 1, wherein the bioactive agent comprises at least one of an antibiotic, antimicrobial, a growth factor, a growth inhibitor, an immunomodulator, a steroid, or an anti-inflammatory.

6. An article comprising a plurality of implantable composites according to claim 1 each comprising a biocompatible polymer film comprising a releasable bioactive agent; and one or more release liners affixed or adhered to each implantable composite.

7. The article of claim 6, wherein the biocompatible polymer film has at least a first surface comprising an adhesive on at least a portion thereof, wherein the release liner is affixed to the adhesive.

8. The article of claim 6, wherein the implantable composite has a length dimension and a width dimension, wherein the length dimension is substantially the same as the width dimension.

9. The article of claim 6, wherein the implantable composite has a shape that is not rectangular.

10. The article of claim 6, wherein the bioactive agent is encapsulated within a microparticle.

11. The article of claim 6, wherein the bioactive agent comprises at least one of an antibiotic, antimicrobial, a growth factor, a growth inhibitor, an immunomodulator, a steroid, or an anti-inflammatory.

12. An implant device having a first implant device surface comprising an implantable composite affixed or adhered to at least a portion of the first implant device surface, wherein the implantable composite comprises a solid tacky biocompatible polymer film comprising a releasable bioactive agent, and a release liner affixed or adhered to the solid tacky biocompatible polymer film, and wherein the solid tacky biocompatible polymer film comprises an adhesive polymer having a $T_g$ less than room temperature and comprises a terpolymer of lactide, glycolide and caprolactone residues, and wherein the amount of lactide residue in the terpolymer is from 10 to 31 mole percent, the amount of glycolide in the terpolymer is from 10 to 40 mole percent, and the amount of caprolactone in the terpolymer is at least 49 mole percent.

13. The implant device of claim 12, wherein the solid tacky biocompatible polymer film is adhered to the implant device surface through the adhesive.

14. The implant device of claim 12, wherein the implantable composite has a length dimension and a width dimension, wherein the length dimension is substantially the same as the width dimension.

15. The implant device of claim 12, wherein the implantable composite has a shape that is not rectangular.

16. The implant device of claim 12, wherein the bioactive agent is encapsulated within a microparticle.

17. The implant device of claim 12, wherein the bioactive agent comprises at least one of an antibiotic, antimicrobial, a growth factor, a growth inhibitor, an immunomodulator, a steroid, or an anti-inflammatory.

* * * * *